United States Patent [19]

Stückler et al.

[11] Patent Number: 4,837,335
[45] Date of Patent: Jun. 6, 1989

[54] PROCESS FOR THE PREPARATION OF PURE 1-PHENYL-3-CARBALKOXY-5-HYDROXYPYRAZOLES

[75] Inventors: Hubert Stückler; Wilhelm Dobramysl, both of Linz, Austria

[73] Assignee: Chemie Linz G.m.b.H., Linz, Austria

[21] Appl. No.: 177,345

[22] Filed: Apr. 4, 1988

[30] Foreign Application Priority Data

Apr. 8, 1987 [DE] Fed. Rep. of Germany ....... 3711878

[51] Int. Cl.$^4$ .......................................... C07D 231/22
[52] U.S. Cl. ................................................... 548/367
[58] Field of Search ........................................ 548/367

[56] References Cited

U.S. PATENT DOCUMENTS 2,457,823  1/1949  Kendall et al. ..................... 260/159

FOREIGN PATENT DOCUMENTS 585780  2/1947  United Kingdom .

Primary Examiner—Robert W. Ramsuer
Attorney, Agent, or Firm—Wenderoth, Lind & Ponack

[57] ABSTRACT

Process for the preparation of pure 1-phenyl-3-carbalkoxy-5-hydroxypyrazoles of the general formula

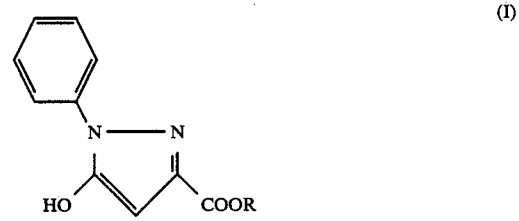

(I)

in which R denotes methyl or ethyl, by reaction of acetylsuccinic esters with phenyldiazonium chloride and a base with $pK_B$ value of 3.6 to $-1.5$ at a pH of 4 to 9 in an aqueous medium to give the corresponding phenylhydrazone, which is cyclized at a pH of 7 to 9.5, with warming and with the addition of ammonia, to give the ammonium salt of the hydroxypyrazole. Compound I is formed by acidification.

9 Claims, No Drawings

PROCESS FOR THE PREPARATION OF PURE 1-PHENYL-3-CARBALKOXY-5-HYDROXYPYRAZOLES

The invention relates to a process for the preparation of pure 1-phenyl-3-carbalkoxy-5-hydroxypyrazoles.

Various hydroxypyrazoles designated in their tautomeric form as pyrazolones are described in US-PS No. 2,457,823. They are used as azo dyestuffs and they are prepared in accordance with the following equation:

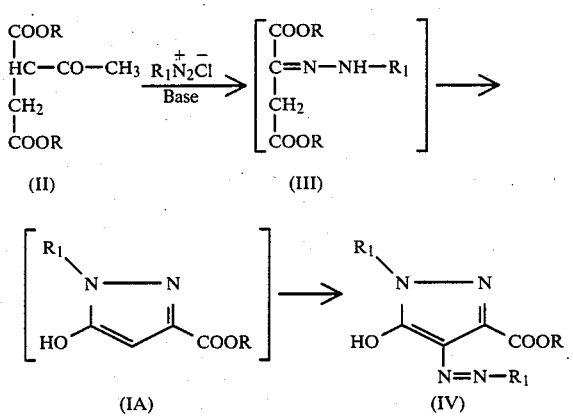

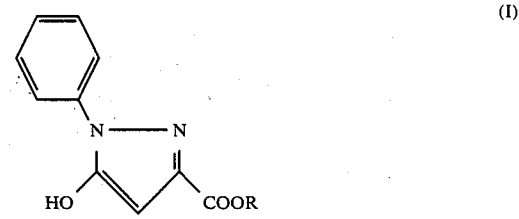

the intermediates stage III and IA not being isolated. However, only those azo dyestuffs of the general formula IV in which the substituent $R_1$ has the same meaning both in the 1-position and in the 4-position of the ring can be prepared by this method. If azo dyestuffs which have different radicals $R_1$ in the 1- and 4-position are to be prepared, it is necessary to isolate the compounds of the general formula IA.

This is described in GB-PS No. 585,780. This specification discloses a process for the preparation of hydroxypyrazoles of the general formula IA, and amongst other things also the preparation of 1-phenyl-3-carbalkoxy-5-hydroxy-pyrazole, by reaction of acetylsuccinic esters with diazonium salts in a basic medium.

When reworking these examples, however, it was found that the yields were only about 20%, and in the specification itself no yields are stated. In GB-PS No. 585,780 itself, it is stated that by-products, such as, for example, the azo dyestuff of the general formula IV, are formed which must be filtered off. A comparison of the melting points given therein with the melting points of the pure compounds also shows that in spite of recrystallization, the product is impure. GB-PS No. 585,780 thus gives the melting point of 1-phenyl-3-carbethoxy-5-hydroxypyrazole as 180° C., whereas the melting point of the pure compound is 183°–184° C.

As can be seen from GB-PS No. 585,780, there are two possibilities for carrying out the reaction. It is carried out either (a) in the presence of weak bases, such as sodium acetate or pyridine, the reaction being brought to completion with a stronger base, such as, for example, sodium carbonate or sodium hydroxide solution, in which case, however, an organic solvent must be used, or (b) in the presence of a strong base, such as, for example, sodium hydroxide solution, from the beginning.

It has now been found, unexpectedly, that the reaction must not be carried out with either a strong base or a weak and then a stronger base and an organic solvent if the product is to be obtained in a yield suitable for an industrial process in combination with a high purity. Rather, pure 1-phenyl-3-carbalkoxy-5-hydroxypyrazole can be obtained in a high yield only if the reaction is carried out in two part steps, the reaction to give the hydrazone of the general formula III being carried out in the presence of an aqueous solution of a base with a $pK_B$ in the range from +3.6 to −1.5 and the cyclization to the hydroxypyrazole of the general formula IA being carried out in the presence of a somewhat weaker base, in particular in the presence of ammonia, the pH being kept substantially constant. No organic solvent is used here.

The invention accordingly relates to a process for the preparation of pure 1-phenyl-3-carbalkoxy-5-hydroxypyrazole of the general formula

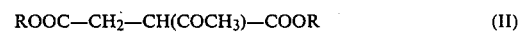

in which R denotes methyl or ethyl, which comprises converting acetylsuccinic esters of the general formula $$ROOC-CH_2-CH(COCH_3)-COOR \qquad (II)$$

in which R has the abovementioned meaning, with simultaneous addition of phenyldiazonium chloride and an aqueous solution of a base with a $pK_B$ value of +3.6 to −1.5 at a pH of 4 to 9, to the phenylhydrazone of the general formula

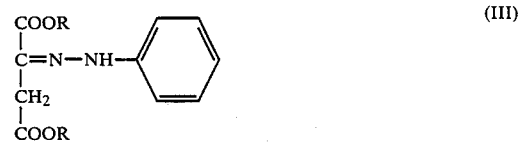

in which R has the abovementioned meaning, and subsequently cyclizing this compound, with warming and with the addition of ammonia at a pH of 7 to 9.5, to give the ammonium salt of the hydroxypyrazole of the general formula I, from which the hydroxypyrazole of the general formula I is liberated by addition of acid.

The process according to the invention is carried out in two part steps in one operation. The nature of the base is adapted to suit the particular part step and the pH is controlled exactly, which means that side reactions are avoided.

In the first part step, an acetylsuccinic ester of the general formula II is coupled with phenyldiazonium chloride, the acetyl radical being split off and the corresponding phenylhydrazone of the general formula III being obtained. Coupling is carried out in the presence of a base with a $pK_B$ of +3.6 to −1.5. Such bases are, for example, sodium carbonate or potassium carbonate with a $pK_B$ of +3.6 or sodium hydroxide solution or potassium hydroxide solution with a $pK_B$ which can also reach negative values down to −1.5, depending on the particular activity.

The reaction is carried out at a pH from about 4 to 9, the range from 7.0 to 8.5 being particularly preferred.

At this pH, the coupling takes place so rapidly that the base added at the same time as the diazonium chloride is consumed immediately and, in practice, virtually no excess of base is present. Decomposition of the diazonium salt and contamination of the phenylhydrazone formed are thereby avoided. At a higher pH, the side reactions get out of control, and at a lower pH the reaction proceeds too slowly. The temperature here is preferably kept at about 10°-30° C., particularly preferably at about 20°-25° C.

According to a preferred embodiment, the acetylsuccinic ester of the general formula II is emulsified in water and an aqueous diazonium chloride solution and an aqueous sodium carbonate solution, which is preferably 10-30% strength, are simultaneously added in the course of 1 to 2 hours such that a pH of about 7.9 to 8.1 is maintained.

Without the phenylhydrazone of the general formula III formed in the first step being isolated, the cyclization to the hydroxypyrazole is carried out in the second part step by warming and adding ammonia, the pH being kept at about between 7.0 and 9.5, preferably between 8.0 and 8.5. The ammonium salt of the hydroxypyrazole of the general formula I is thereby formed, without side reactions taking place. The ammonium salt can be obtained by adding aqueous ammonia in various concentrations, for example 20-30% strength, or also by passing in gaseous ammonia. The addition of the ammonia is carried out continuously at the rate at which the ammonium salt of the hydrox. pyrazole forms. The end of the reaction is indicated by an increase in the pH. The cyclization is carried out at a temperature of about 40°-80° C., preferably at about 55°-65° C.

The hydroxypyrazole of the general formula I is liberated from the ammonium salt. The liberation is effected by addition of an acid, in particular by adding mineral acids, such as, for example, hydrochloric acid.

The product is thereby obtained in a yield of at least 94% and has a purity of 99.5%.

It can be used to prepare pure azo dyestuffs, which can be built up either symmetrically (the substituents $R_1$ of the ring in positions 1 and 4 in the general formula IV are identical) or unsymmetrically (the substituents $R_1$ of the ring in positions 1 and 4 in the general formula IV are not identical).

EXAMPLE 1

(a) Phenyldiazonium chloride 93.1 g (1 mole) of aniline were initially introduced into 250 ml of water and 557 ml of 35% strength hydrochloric acid and a solution of 69 g (1 mole) of sodium nitrite in 250 ml of water was added dropwise at 0° C., with stirring.

(b) Diethyl phenylhydrazonesuccinate 216 g (1 mole) of diethyl acetylsuccinate were emulsified in 300 ml of water and the phenyldiazonium chloride solution described under (a) was added at 20° to 25° C. in the course of one and a half hours. An aqueous 20% strength sodium carbonate solution was added at the same time such that a pH of 8.0 was maintained.

(c) 1-Phenyl-3-carbethoxy-5-hydroxypyrazole

The emulsion obtained under (b) was heated to 60° C. and 25% strength aqueous ammonia was added continuously so that a pH of 8.2 to 8.4 was maintained. After filtration from traces of undissolved components, the resulting ammonium salt of 1-phenyl-3-carbethoxy-5-hydroxypyrazole was precipitated by addition of hydrochloric acid, filtered off, washed with water and dried. Yield: 220 g (95%); melting point: 183°-184° C.; content: 99.5% (potentiometric bromate titration).

EXAMPLE 2

Starting from 188 g (1 mole) of dimethyl acetylsuccinate, 1-phenyl-3-carbomethoxy-5-hydroxypyrazole was prepared in the same manner as in Example 1. Yield: 205 g (94%); melting point: 197°-198° C.; content: 99.5% (potentiometric bromate titration).

We claim:

1. A process for the preparation of a pure 1-phenyl-3-carbalkoxy-5-hydroxypyrazole of the general formula

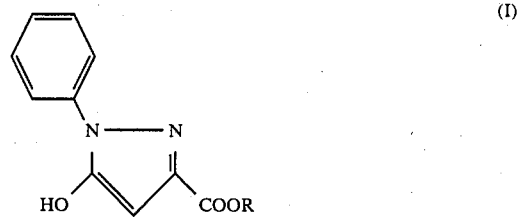

in which R denotes methyl or ethyl, which comprises converting an acetylsuccinic ester of the general formula

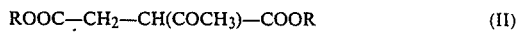

in which R has the abovementioned meaning, with simultaneous addition of phenyldiazonium chloride and an aqueous solution of a base with a $pK_B$ value of $+3.6$ to $-1.5$ at a pH of 4 to 9, to the phenylhydrazone of the general formula

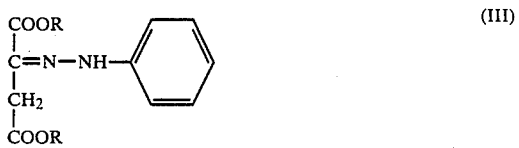

in which R has the abovementioned meaning, and subsequently cyclizing this compound, with warming and with the addition of ammonia at a pH of 7 to 9.5, to give the ammonium salt of the hydroxypyrazole of the general formula I, from which the hydroxypyrazole of the general formula I is liberated by addition of acid.

2. The process as claimed in claim 1, wherein the acetylsuccinic ester of the general formula II is reacted with phenyldiazonium chloride and an aqueous 10 to 30% strength sodium carbonate solution.

3. The process as claimed in claim 1, wherein a pH of 7 to 8.5 is maintained during the preparation of the phenylhydrzone of the general formula III.

4. The process as claimed in claim 1, wherein a pH of 7.9 to 8.1 is maintained during the preparation of the phenylhydrazone of the general formula III.

5. The process as claimed in claim 1, wherein a temperature of 10° to 30° C. is maintained during the preparation of the phenylhydrazone of the general formula III.

6. The process as claimed in claim 1, wherein the cyclization to give the ammonium salt of the hydroxypyrazole of the general formula I is carried out by addition of 20 to 30% strength aqueous ammonia.

7. The process as claimed in claim 1, wherein the cyclization to give the ammonium salt of the hydroxypyrazole of the general formula I is carried out at a temperature of 40° to 80° C.

8. The process as claimed in claim 1, wherein the cyclization to give the ammonium salt of the hydroxypyrazole of the general formula I is carried out at a temperature of 55° to 65° C.

9. The process as claimed in claim 1, wherein the cyclization to give the ammonium salt of the hydroxypyrazole of the general formula I is carried out at a pH of 8 to 8.5.

* * * * *